United States Patent [19]

Epplen

[11] Patent Number: 4,987,066
[45] Date of Patent: Jan. 22, 1991

[54] PROCESS FOR THE DETECTION OF RESTRICTION FRAGMENT LENGTH POLYMORPHISMS IN EUKARYOTIC GENOMES

[75] Inventor: Jörg T. Epplen, Freiburg, Fed. Rep. of Germany

[73] Assignee: Max Planck-Gesellschaft Zur Forderung der Wissenschaften E.V., Fed. Rep. of Germany

[21] Appl. No.: 101,218

[22] Filed: Sep. 25, 1987

[30] Foreign Application Priority Data

Nov. 7, 1986 [EP] European Pat. Off. ........ 86115460.7

[51] Int. Cl.⁵ .................... C12Q 1/68; C07H 15/12; C12N 15/00
[52] U.S. Cl. ........................................ 435/6; 536/27; 935/77; 935/78
[58] Field of Search .............. 435/6; 935/77, 78; 536/27

[56] References Cited

FOREIGN PATENT DOCUMENTS 2188323 9/1987 United Kingdom .
2166445 11/1987 United Kingdom .

OTHER PUBLICATIONS

Jeffreys et al., Nature, vol. 316, 76-79, 1985.
Schäfer et al., Chromosoma 93, 496-501, 1986.
White, R., Trends Genet 1:177-181 (1985).
Jeffreys, A. J., et al., Nature 314:67-73 (1985).
Jeffreys, A. J., et al., Nature 317:818-819 (1985).
Epplen, J. T., et al., Proc. Natl. Acad. Sci. U.S.A. 79:3798-3802 (1982).
Schäfer, R., et al., Chromosoma 93:502-510 (1986).
Kunkel, L. M. et al., Proc. Natl. Acad. Sci. U.S.A. 74:1245-1249 (1977).
Bell, G. I., et al., Nature 295:31-35 (1982).

Primary Examiner—Robert A. Wax
Assistant Examiner—Mindy Fleisher
Attorney, Agent, or Firm—Sterne, Kessler, Goldstein & Fox

[57] ABSTRACT

The invention is directed to a process for the analysis of eukaryotic DNA wherein DNA of an individual is isolated, the DNA is subjected to restriction endonuclease digest, the cleaved DNA is separated by gel electrophoresis, the gel is dried and hybridized with a probe, and the pattern of the DNA is evaluated. The process is characterized in that the probe used is an oligonucleotide which specifically hybridizes to eukaryotic simple tandem repeats having a periodicity of 2 to 4 bases.

The process of the invention may be employed for the in vitro diagnosis of genetic defects such as hereditary diseases or for the determination of the genetic interrelationships.

26 Claims, 6 Drawing Sheets

PROCESS FOR THE DETECTION OF RESTRICTION FRAGMENT LENGTH POLYMORPHISMS IN EUKARYOTIC GENOMES

BACKGROUND OF THE INVENTION

It is known that the human genome contains about $10^7$ to $3 \times 10^7$ polymorphic loci. Studies on human genetic variation have been substantially enhanced by the exploitation of restriction fragment length polymorphisms (RFLPs).

Several hundred probes detecting RFLPs have been characterized; most probes stem from the systematic searches of arbitrarily cloned DNA segments or from chromosome-specific libraries.

Generally, these human genetic markers detect single base exchanges of single copy sequences (Botstein et al., 1980). Yet, these several hundred probes are still not sufficient to allow for the identification of sufficient RFLPs which cover the human genome in short genetic intervals (about 10 cM). The human genome, however, contains unique repetitive DNA. Tandemly organized simple repetitive DNA which is interspersed frequently in the genome also shows base sequence polymorphisms. These RFLPs probably arise from unequal exchanges altering the number of tandem repeats in a given DNA fragment. Since numerous variants exist, many alleles can be defined. Because of the numbers and frequencies of their alleles, regions of interspersed simple repetitive DNA are regarded as the most informative genetic markers (White 1985). Taking advantage of certain interspersed repetitive DNAs, the so-called mini-satellites, Jeffreys and co-workers (1985 a, b, c) developed the principle of "DNA fingerprinting": cloned probes based on a core of tandemly repeated sequences that can detect many highly variable loci simultaneously and hence provide highly individual-specific hybridization patterns.

Another family of simple repeats, the GA A sequences, has originally been identified and isolated from female-specific snake satellite DNA (Epplen et al., 1982a). Subsequently, it was found that these Simple Quadruplet Repeats (sqr) are conserved throughout the eukaryotes. In the human and the murine genomes the sqr are interspersed throughout the entire chromosomal complement (Epplen et al., 1982b; Schäfer et al., 1986a). These properties qualify the sqr as candidates for RFLP studies.

DESCRIPTION OF THE INVENTION

The problem underlying the present invention is to provide a process for the detection of RFLPs in eukaryotic genomes, particularly in the human genome, which is not limited to the detection of single base exchanges of single copy sequences but allows the simultaneous detection of many RFLPs in a eukaryotic genome and particularly in the human genome.

The solution of this technical problem is achieved by providing a DNA fingerprinting process in which oligonucleotides, being specific for simple tandem repeats having a periodicity of 2 to 4 bases, are used as probes.

This solution is based on the above-mentioned finding that the simple tandem repeats having a periodicity of 2 to 4 bases are the most informative genetic markers which are conserved throughout the genomes of eukaryotes.

The subject matter of the invention therefore is a process for the analysis of eukaryotic DNA wherein DNA of an individual is isolated, the DNA is subjected to restriction endonuclease digest, the cleaved DNA is separated by gel electrophoresis, the gel is dried and hybridized with a probe, and the pattern of the DNA is evaluated, said process being characterized in that the probe used is an oligonucleotide which specifically hybridizes to eukaryotic simple tandem repeats having a periodicity of 2 to 4 bases.

Under appropriate hybridizing conditions, oligonucleotide probes are absolutely specific such that a single base mismatch will obstruct the hybridization (Itakura et al.. 1984). In view of these considerations, tandem repeat probes of varying lengths were used.

One specific subgroup of the simple tandem repeats used in the method of the present invention are the repetitive quadruplet sequences (sqr), especially the repetitive and $GA_C^TA$ and GGAT sequences.

It was found that the GATA-20-mer is the optimal length, for it revealed the maximum number of discernible bands. The 23-mer GATA probe showed a reduced number of bands in all four digests, suggesting that probably an increase in the probe length produces mismatches and consequently reduces the overall hybridization. Thus, in several bands produced by Alu I digestion, e.g., uninterrupted GATA stretches are clearly more than 16 bases long but certainly less than 24 nucleotides.

Another subgroup of simple tandem repeats which is applicable in the method of the present invention is repetitive triplet sequences. A special example for this subgroup is the sequence $(TCC)_5$.

Still another subgroup of simple tandem repeats that may be used in the method of the present invention is the repetitive doublet sequences of which the sequences $(GT)_8$ and $(CT)_8$ are specific examples.

The advantages of "mini-satellite" probes over traditional RFLP probes have been discussed in detail (Jeffreys et al., 1985 a, b, c). All of these favorable points can also be scored by oligonucleotide probes as exemplified here. In addition, quantitative differences (band intensities) can be evaluated. Furthermore, oligonucleotide hybridization is much faster, and exposure time is approximately one-sixth of classical "mini-satellite" probes. Taken together, oligonucleotides specific for simple repeated DNA is to be considered a valuable alternative probe in most RFLP studies.

The process of the invention is applicable to the analysis of eukaryotic DNA in general. It may advantageously be used for the analysis of mammalian, especially human, DNA. Specific examples for the restriction enzymes to be used in the process are Alu I, Hae III, Hinf I, and Mbo I.

The preferred simple quadruplet repeats (sqr) recognized by the oligonucleotide probe in the eukaryotic genome and $GA_C^TA$ sequences or their complement sequences $T_G^ATC$.

The quadruplet oligonucleotide used in the process preferably has a length of 16 to 23 nucleotides; more preferable are 20-mers. Specific examples of quadruplet-oligonucleotides to be used in the process are $(GATA)_4$, $(GACA)_4$, $(GATA)_4GA$, $(GATA)_5$, and $(GATA)_2GACA(GATA)_2$ as well as the complement sequences thereof, i.e., the sequences $(TATC)_4$, $(TGTC)_4$, $TC(TATC)_4$, $(TATC)_5$, and $(TATC)_2TGTC(TATC)_2$.

The subject matter of the invention also includes all quadruplet-oligonucleotides having the sequences as mentioned above but beginning with any one of the other nucleotides. For example with (TATC)$_4$, these sequences include: ATC(TATC)$_3$T, TC(TATC)$_3$TA, and C(TATC)$_3$TAT and the complement sequences thereof.

A further preferred example of the quadruplet oligonucleotides is the sequence (GGAT)$_4$ and its complement sequence (ATCC)$_4$ including all sequences beginning with any one of the other nucleotides.

The triplet-oligonucleotides used have preferably a length of 15-24 bases; more preferable are 15-mers. A specific example used in the process is (TCC)$_5$ as well as the complement thereof (GGA)$_5$. The subject matter of the invention also includes all triplet-oligonucleotides having the sequence mentioned above but beginning with any one of the other bases, i.e., CC(TCC)$_4$T, C(TCC)$_4$TC, and the complement sequences thereof.

The doublet-oligonucleotide probes used also have preferably a length of 16-24 bases; more preferable are 16-mers. Specific examples are (CT)$_8$ and (GT)$_8$ as well as the complement thereof (GA)$_8$ and (CA)$_8$. The subject matter of the invention also includes all doublet-probes having the sequence mentioned above but beginning with the other base, i.e., T(CT)$_7$C and T(GT)$_7$G and the complement sequences thereof.

The process of the invention can be employed for the in vitro diagnosis of genetic defects such as hereditary diseases or for the determination of the genetic interrelationships.

Figure 1A:
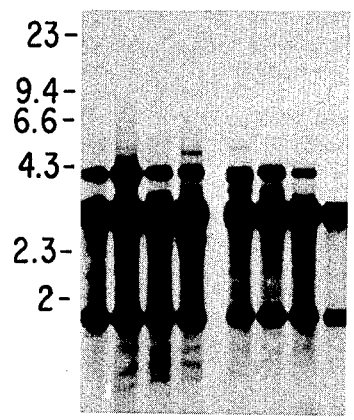
FIG. 1: Gel hybridization of MboI digested human DNA from eight individuals. The same gel was hybridized consecutively with the following probes at the indicated hybridization temperatures: (a) (GACA)$_4$, 43° C.; (b) (GATA)$_4$, 35° C.; (c) (GATA)$_4$GA, 41° C.; (d) (GATA)$_5$, 45° C.; (e) (GATA)$_5$GAT, 53° C.; (f) (GATA)$_2$ GACA (GATA)$_2$, 47° C. The washed gel was exposed to Kodak XAR-5 film without intensifying screen for at least 16 hours. After each exposure, probes were removed by the denaturation/neutralization procedure and the gel was washed in 5 mM EDTA (pH 7) at 60° C. Washing efficiency was monitored by control exposures. Molecular weight markers are given on the left in kilobases.

Note the related banding patterns in the CT-, GACA- and GA$_C^T$A-hybridizations. The GT- and TCC-oligonucleotides detect even more polymorphic bands than the quadruplet repeat probes. Molecular weight markers are indicated by the horizontal bars in kilobases. For further details see Materials and Methods. Symbols: male; female; offspring.

The following examples are presented to illustrate the invention and are not intended to be limiting.

EXAMPLE 1

A. Materials and Methods

DNA was isolated from the peripheral blood of ten unrelated and four related donors according to Kunkel et al. (1977) with minor modifications. The unrelated individuals studied were normal and included seven Caucasians (five Germans, two British), two Asians (from India), and one black African (from Ethiopia). The four related donors took part in a screening program for RFLP analysis. Three to five micrograms of each individual's DNA was digested with the restriction enzymes Alu I, Hae III, Hinf I, and Mbo I according to the manufacturer's recommendations. Control digestions were performed with plasmid DNA added to the samples of human DNA to ensure completeness of the digestions. Electrophoresis was carried out in 0.6% agarose gels in TAE buffer (40 mM Tris, 12 mM Na acetate, 2 mM EDTA; pH 8.3). The gels were blotted dry on a vacuum-gel dryer for one hr at ambient temperature and one hr at 60° C. (Tsao et al., 1983). Prior to hybridization, gels were denatured in 0.5 M NaOH/0.15 M NaCl for 30 min and neutralized in 0.5 M Tris/0.15 M NaCl (pH 8) for 30 min at room temperature. The oligonucleotide probes were labeled in a standard kinase reaction (Schäfer et al., 1986a) using 32$_P$-gATP.

Hybridizations were carried out at the temperatures indicated below for 4-5 hr in 5×SSPE (1×SSPE=180 mM NaCl, 10 mM Na$_{1.5}$PO$_4$, 1 mM EDTA; pH 8.0), 0.1% SDS 10 μg/ml sonicated and denatured E. coli DNA and 1×10$^6$ cpm/ml of the labeled probes: (GACA)$_4$, 43° C.; (GATA)$_4$, 35° C.; (GATA)$_4$GA, 41° C.; (GATA)$_5$, 45° C.; (GATA)$_5$GAT, 53° C.; and (GATA)$_2$GACA(GATA)$_2$, 47° C. in hybridization the given temperatures should be adhered to within a range of deviation of ±2° C. This also applies for all the other probes used according to the invention. After hybridization, gels were washed on ice in 6×SSC (20×SSC: 175.3 g NaCl; 8.82 g Na citrate per liter) followed by a one min wash at the hybridizing temperature, respectively. Gels were exposed to Kodak XAR-5 X-ray films without intensifying screen. In order to reprobe the gels, probes were removed by treating the gels as for denaturation and neutralization mentioned earlier and by two washes 15 min each in 5 mM EDTA (pH 7) at 60° C. and finally treating the gels with 6×SSC for 20 min at room temperature.

In order to estimate copy number variations in the individual DNA samples, the plasmids pmlc 2 and pmcl 4 (Schäfer et al., 1986b) were included in the gel electrophoresis. These plasmids contain known stretches of GATA and GACA repeats. On the basis of several concentrations of the plasmids and their signal intensity differences, copy numbers in the human genomic DNA were estimated.

The demonstration of DNA fingerprints using oligonucleotide probes may also be effected with the Biotin/Streptavidin-labeling method. Though this method is less sensitive as compared to $^{32}$P-labeling, banding patterns are readily visible. This is because multiple probe molecules hybridize to each polymorphic DNA fragment (because of the tandem repetitive character of the simple repeat sequences detected). The applicability of a non-radioactive method is demonstrated by synthesizing biotinylated oligonucleotide probes (e.g., according to the method described by Agrawe et al., *Nucleic Acids Research* 14:6227 (1986)). The advantages of non-radioactive detection methods are obvious.

B. Results

Rationale of the probe design

The simple repetitive GA$_C^T$A sequences were detected originally in sex-specific satellite DNA and subsequently found to be organized sex-specifically in the mouse as well (Epplen et al.. 1982b). In view of the interspersion of GA$_C^T$A sqr on human autosomes and sex chromosomes (Epplen et al., 1982a), we have used (GACA)$_4$ and (GATA)$_4$ oligonucleotide probes to monitor RFLPs in the human genome. In order to evaluate the effect of the probe length, four different GATA-oligonucleotides (16–23 mers) were synthesized on an automated DNA synthesizer (Applied Biosystems #381A). Both sqr GATA and GACA are contained in the more complex probe (GATA)$_2$GACA(GATA)$_2$.

GA$_C^T$A sequences detect many RFLPs.

To analyze the DNA variation, all individual human DNA samples were digested and hybridized with the probes listed in Materials and Methods. An example of the serial hybridization results is illustrated in FIG. 1. Since GA$_C^T$A sqr are present in copy numbers up to $10^4$ in eukaryotic genomes (Schäfer et al., 1986a), a multitude of hybridizing bands was expected. These signals cannot be resolved in conventional agarose gel electrophoreses and therefore form smears in the short fragment sizes (<1 kb). But in the higher molecular weight range, a number of bands are clearly distinguishable. Some bands are common to all individual DNAs, others are present only in a certain percentage of the samples.

The results obtained in the hybridization experiments are summarized in Table I and will be discussed hereinafter in more detail.

TABLE I

DNA variation between random pairs of individuals (n = 10).

| | Enzymes | | | |
|---|---|---|---|---|
| | Alu I | Hae III | Hinf I | Mbo I |
| Number of common different bands with the probes | | | | |
| (GACA)$_4$ | 4/29 | 5/11 | 5*/14* | 5/20 |
| (GATA)$_5$ | 4/18 | 4/19 | 4*/17* | 7/26 |
| (GATA)$_2$GACA(GATA)$_2$ | 5/20 | 4/15 | 12*/6* | 9*/13* |
| Average number of different bands per individual with the probes | | | | |
| (GACA)$_4$ | 2.9 | 1.1 | 1.8 | 2 |
| (GATA)$_5$ | 1.8 | 1.9 | 2.1 | 2.6 |
| (GATA)$_2$GACA(GATA)$_2$ | 2.0 | 1.5 | 0.75 | 1.6 |
| Mean probability P that the band pattern in A is also present in B (maximum mean allelic frequency) | | | | |

TABLE I-continued

DNA variation between random pairs of individuals (n = 10).

| | Enzymes | | | |
|---|---|---|---|---|
| | Alu I | Hae III | Hinf I | Mbo I |
| (GACA)$_4$ | 0.65 | 0.39 | 0.58* | 0.55 |
| | (0.41) | (0.22) | (0.35)* | (0.33) |
| (GATA)$_5$ | 0.33 | 0.64 | 0.33* | 0.36 |
| | (0.18) | (0.40) | (0.18)* | (0.20) |
| (GATA)$_2$GACA(GATA)$_2$ | 0.56 | 0.51 | 0.33* | 0.49* |
| | (0.34) | (0.30) | (0.18)* | (0.29)* |

*Based on eight individuals only.

Figure 1B:
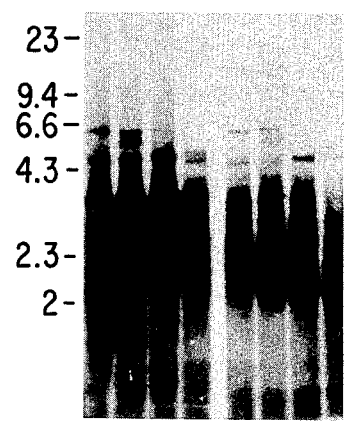
Figure 1C:
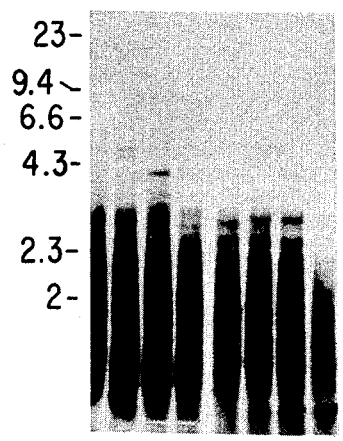
Figure 1D:
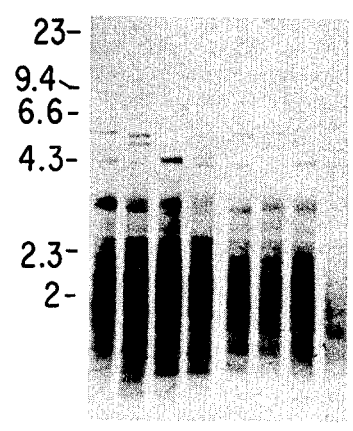
Figure 1E:
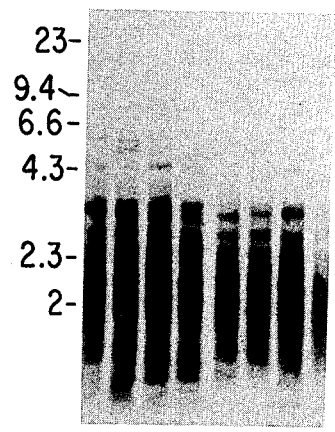
Figure 1F:
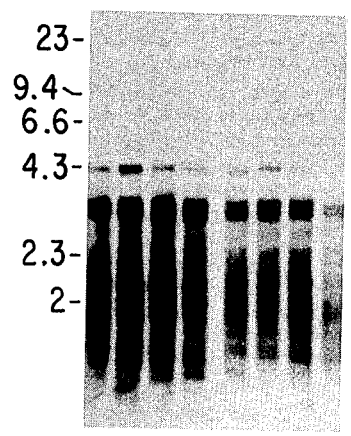

In Table I only such bands were scored that were clearly discernible. For example, Mbo I digested DNA yields five common bands with the (GACA)$_4$ probe, while six bands appear only in a subset of the individuals (FIG. 1a). The four GATA probes hybridize in similar patterns to the DNAs (FIG. 1b, c, d, e). From these, the (GATA)$_5$ probe reveals the maximum of discernible bands in all digestions. In the Mbo I digestion seven bands are identified in all the DNAs, 13 bands are unique or shared by a few individuals only. The mixed sqr probe shows more common than different bands. Using the three principally differing probes listed in Table I, the highest numbers of uncommon bands was seen in the Alu I and Mbo I digestions. By employing these three probes and the two enzymes, a probability can be estimated to find identical patterns in two unrelated individuals. An average number of bands per individual was determined for each probe/enzyme combination, and the mean allele frequency was calculated. From Table I, the probability P is derived to find the pattern of individual A also in an unrelated person B: $(0.65)^{2.0} \times (0.33)^{1.8} \times (0.56)^2 \times (0.55)^2 \times (0.36)^{2.6} \times (0.49)^{1.6} \times 8 \times 10^{-5}$ (for details, see legend to Table I). It should be noted that the mean probabilities in Table I represent maximum mean allelic frequencies on the basis of 8–10 individuals. By increasing the number of DNAs tested, these frequencies are likely to be reduced: in a preliminary experiment we tested an additional panel of 14 German individuals with the (GATA)$_5$ probe; the mean probability P that the band in individual A is also present in B is 0.29. The number of different bands per individual is increased to 2.9.

Since oligonucleotide hybridization is virtually absolutely specific, significant intensity differences of the individual co-migrating bands can also be scored. Some of the common bands did not show significant intensity variations and can therefore serve as inherent controls for the DNA amount loaded onto the gel. In our panel of eight to ten DNAs, however, about half of the common bands of all individuals show considerable intensity variations in one or more samples. These variations represent changing numbers of exact sqr copies. Compared to plasmid control DNA of known sqr content, copy numbers vary in the DNAs by up to three orders of magnitude. Thus, the probability estimate that all fragments detected in A are also present in equal intensity in B is reduced by at least a factor of 2 ($= <4 \times 10^{-5}$).

Figure 2C:
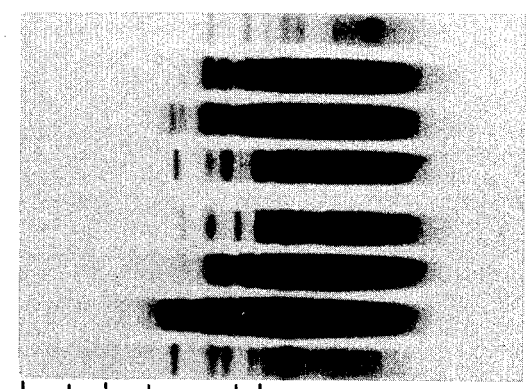
FIG. 2: Gel hybridization of Alu I digested human DNA from eight individuals. The same gel was hybridized consecutively with the six probes described in FIG. 1; only two hybridization patterns are shown here: (a) ethidium bromide staining; (b) (GATA)$_4$; (c) (GATA)$_5$. For methodological details, see Materials and Methods and the legend of FIG. 1. Molecular weight markers are given in kilobases on the left. Note the differences in signal intensities of co-migrating bands.
Figure 2B:
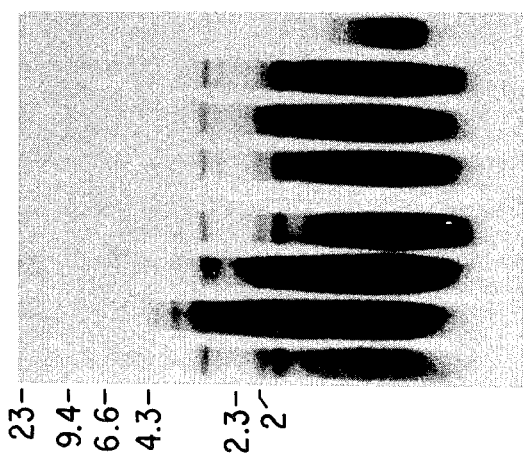
Figure 2A:
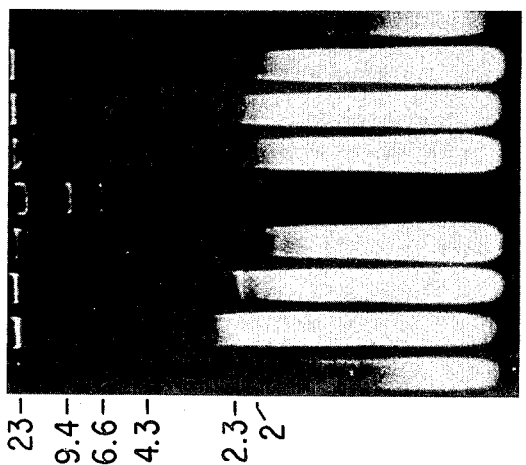
Figure 3:
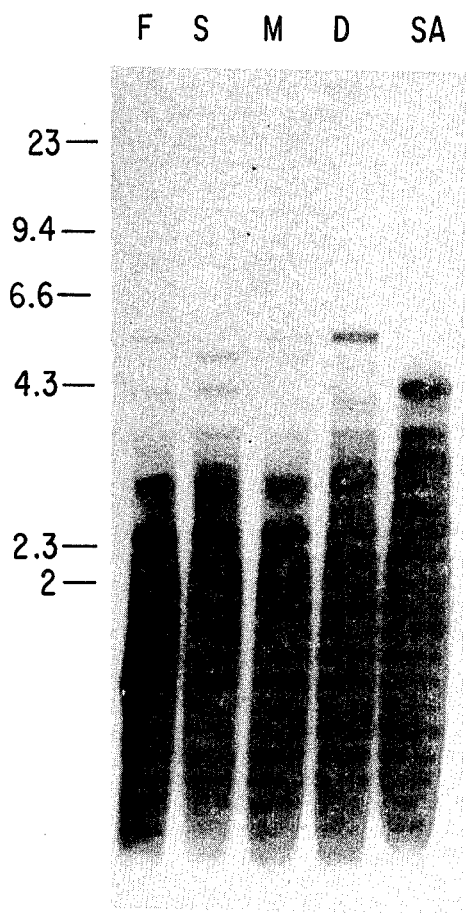
FIG. 3: Gel hybridization analysis of MboI digested DNA of four family members (F, father; S, son; M, mother; D, daughter) with the oligonucleotide probe (GATA)$_5$. Molecular weight markers are given in kilobases on the left; the lane on the right contains DNA of an unrelated individual (SA). For methodological details see Materials and Methods.
Figure 4A:
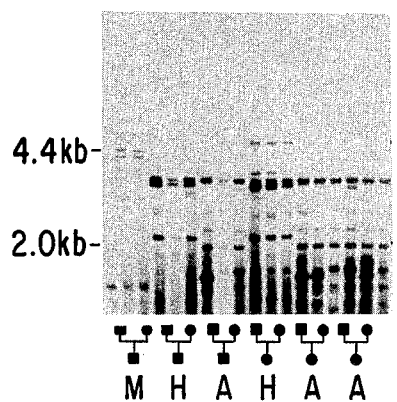
FIG. 4: Comparison of the oligonucleotide probes used for DNA fingerprinting of human DNA. DNA of seven families (for the pedigrees, see bottom) was digested with the restriction enzymes Mbo I (M), Hinf I (H), and Alu I (A). DNA samples were digested and the gel dried. The same gel was hybridized consecutively with the following seven probes [at the temperatures indicated]: (a) (CT)$_8$. [43° C., abbreviated CT]; (b) (GACA)$_4$ [43° C., abbreviated GACA]; (GATA)$_2$ GACA (GATA)$_2$ [47° C., abbreviated GA$_C^T$A]; (d) (GATA)$_4$ [35° C., abbreviated GATA]; (e) (GGAT)$_4$ [43° C., abbreviated GGAT]; (f) (GT)$_8$ [43° C., abbreviated GT]; and (g) (TCC)$_5$ [45° C., abbreviated TCC].
Figure 4B:
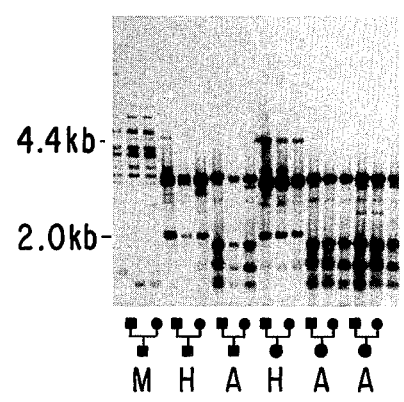
Figure 4C:
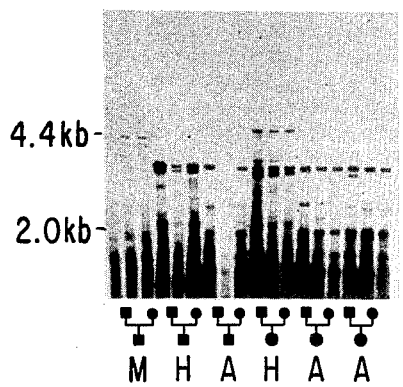
Figure 4D:
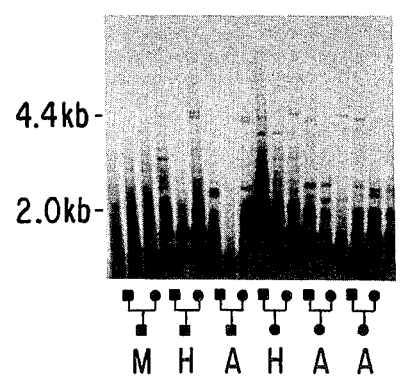
Figure 4E:
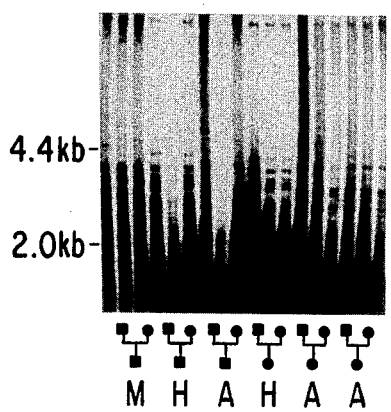
Figure 4F:
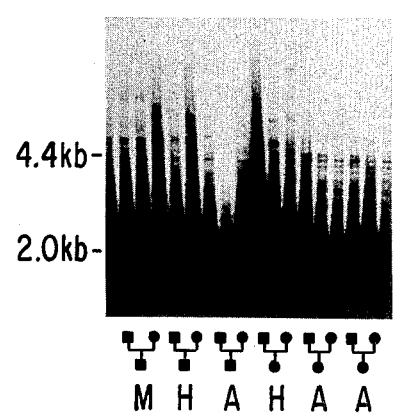
Figure 4G:
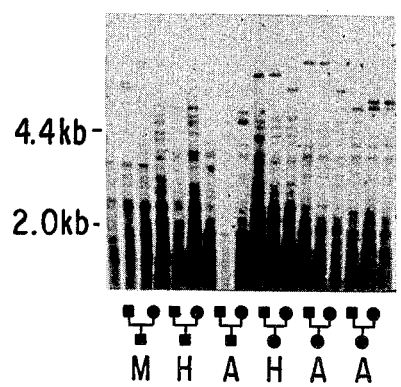

The effect of the length of the probe is demonstrated in FIG. 2. Increasing probe length changes band intensities though the same bands are present. The hybridized gel in FIG. 2b has been exposed for 12 hrs while exposure time for FIG. 2c was 36 hrs. Comparatively reduced band intensity of the common band in all DNAs (arrow) with the longer probes indicates that respective sqr are organized in stretches shorter than 20 or 23 bases, respectively (see also FIG. 1). In family studies, Mendelian inheritance of the sqr banding patterns was confirmed (see FIG. 3). As with the conventional nick-translated sqr probe, no consistent sex-specific bands were observed in any of the digestions with any oligonucleotide probe.

By investigating more than hundred meiotic events in more than 50 families, it could be established that the mutation rate affecting DNA fragment mobility is less than 2% using the GA A oligonucleotide probes. This comparatively low m rate for simple tandem repeats represents a remarkable advantage over the fingerprinting methods according to Jeffreys et al. (1985).

EXAMPLES 2 TO 4

Similar DNA fingerprint patterns (as the ones described above) have been obtained using the oligonucleotide probe (GGAT)$_4$ or probes with even shorter periodicity like, e.g., (TCC)$_5$, (GT)$_8$, and (CT)$_8$ (see FIG. 4). Methodological details are given in the figure legend and the Materials and Methods section of Example 1 It is evident from FIG. 4 that the (GT)$_8$ and (TCC)$_8$ probes detect even more polymorphic bands, thus reducing the necessity to employ different enzymes and probes for individual-specific fingerprints.

Although the foregoing invention has been described in some detail by way of illustration and example for purposes of clarity and understanding, it will be obvious that certain changes and modifications may be practiced within the scope of the invention, as limited only by the scope of the appended claims.

REFERENCES

Botstein D., White R. L., Skolnick M., Davis R. W. (1980), Construction of a genetic linkage map in man using restriction fragment length polymorphisms, *Am. J. Hum Genet.* 32:314-331

Epplen J. T., Sutou S., McCarrey J. R. and Ohno S. (1982a) Is sex specifically arranged repetitive DNA involved in primary sex determination in vertebrates. In: Bonnetamir B (ed) Human Genetics Part A: The Unfolding Genome. Alan R. Liss, New York, pp. 317-326

Epplen J. T., McCarrey J. R., Suton S., Ohno S. (1982b) Base sequence of a cloned snake W-chromosome DNA fragment and identification of a male specific putative mRNA in the mouse. *Proc. Natl. Acad. Sci. USA* 79:3798-3802

Itakura K., Rossi J. J., Wallace R. B. (1984) Synthesis and use of synthetic oligonucleotides. *Ann. Rev. Biochem.* 53:323-356

Jeffreys A. J., Wilson V., Thein S. L. (1985a) Hypervariable "minisatellite" regions in human DNA. *Nature* 314:67-73

Jeffreys A. J., Wilson V., Thein S. L. (1985b) Individual-specific "fingerprints" of human DNA. *Nature* 316:76-79

Jeffreys A. J., Brookfield J. F. Y., Semeonoff R. (1985c) Positive Identification of an immigration testcase using human DNA fingerprints. *Nature* 317:818-819

Kunkel L. M., Smith K. D., Boyer S. H., Borgaonkar D. S., Wachtel S. S., Miller O. J., Breg W. R., Jr. Jones H. W., Rary J. M. (1977) Analysis of human Y chromosome-specific reiterated DNA in chromosome variants. *Proc Natl Acad Sci. USA* 74:1245-1249

Schafer R., Ali S., Epplen J. T. (1986a) The organization of the evolutionarily conserved GATA/GACA repeats in the mouse genomes. *Chromosoma* 93:502-510

Schafer R., Böltz E., Becker A., Bartels F., Epplen J. T. (1986b) The expression of the evolutionarily conserved GATA/GACA repeats in mouse tissue. *Chromosoma* 93:496-501

Tsao S. G. S., Brunk C. F., Perlman R. E. (1983) Hybridization of nucleic acids directly in agarose gels. *Analyt Biochem.* 131:365-372

White R. (1985) DNA sequence polymorphisms revitalize linkage approaches in human genetics. *Trends Genet.* 1:177-181

I claim:

1. In a process for the determination of the genetic interrelationships of individuals comprising analysis of eukaryotic DNA wherein DNA of an individual is isolated, the DNA is subjected to restriction endonuclease digests, the cleaved DNA is separated by gel electrophoresis, the gel is dried and hybridized with a probe, and the pattern of the DNA is evaluated and compared to that of other individuals, the improvement which comprises use of a probe which comprises a chemically synthesized oligonucleotide which specifically hybridizes to eukaryotic simple tandem repeats having a periodicity of 2 to 4 bases.

2. The process according to claim 1, characterized in that the DNA used is human or animal DNA.

3. The process according to any one of claims 1 and 2, characterized in that the restriction enzyme used is Alu I, Hae III, Hinf I, or Mbo I.

4. The process according to claim 1, characterized in that the probe used is an oligonucleotide which specifically hybridizes to eukaryotic simple quadruplet repeats (sqr).

5. The process according to claim 4, characterized in that the simple quadruplet repeats (sqr) recognized by the oligonucleotide probe in the eukaryotic genome are $GA^A_CA$ sequences or their complement sequences $T^A_GTC$.

6. The process according to claim 5, characterized in that the oligonucleotide has a length of 16 to 23 nucleotides.

7. The process according to claim 6, characterized in that the oligonucleotide is (GATA)$_4$GA or its complement sequence TC(TATC)$_4$.

8. The process according to claim 6, characterized in that the nucleotide is a 20-mer.

9. The process according to claim 6, characterized in that the oligonucleotide is (GATA)$_5$ or its complement sequence (TATC)$_5$.

10. The process according to claim 6, characterized in that t he oligo nucleotide is (GATA)$_2$GACA(GATA)$_2$ or its complement sequence (TATC)$_2$TGTC(TATC)$_2$.

11. The process according to claim 6, characterized in that the oligonucleotide is (GATA)$_4$, (GACA)$_4$, or their complement sequences (TATC)$_4$ or (TGTC)$_4$.

12. The process according to claim 6, characterized in that the oligonucleotide is (GGAT)$_4$ or its complement sequence (ATCC)$_4$.

13. The process according to claim 1, characterized in that the probe used is an oligonucleotide which specifically hybridizes to eukaryotic simple triplet repeats.

14. The process according to claim 13, characterized in that the simple triplet repeats recognized by the oligonucleotide probe in the eukaryotic genome are TCC sequences or their complement sequences GGA.

15. The process according to claim 14, characterized in that the oligonucleotide has a length of 15 to 24 nucleotides.

16. The process according to claim 15, characterized in that the oligonucleotide is (TCC)$_5$ or its complement sequence (GGA)$_5$.

17. The process according to claim 1, characterized in that the probe used is an oligonucleotide which specifically hybridizes to eukaryotic simple doublet repeats.

18. The process according to claim 17, characterized in that the simple duplet repeats recognized by the oligonucleotide probe in the eukaryotic genome are GT sequences or their complement sequences AC.

19. The process according to claim 18, characterized in that the oligonucleotide has a length of 16 to 24 nucleotides.

20. The process according to claim 19, characterized in that the oligonucleotide is (GT)$_8$ or its complement sequence (AC)$_8$.

21. The process according to claim 19, characterized in that the oligonucleotide is (CT)$_8$ or its complement sequence (AG)$_8$.

22. The process according to claim 1, characterized in that the consecutive hybridization and evaluation operation comprises hybridizing the cleaved DNA with the radioactively labeled probe, removing the unhybridized part of the probe, exposing an X-ray film to the hybridized product, removing the hybridized product from the gel and repeating the operation with another probe.

23. The process according to claim 1, characterized in that the hybridization and evaluation operation comprises transferring the cleaved DNA onto a solid support, hybridizing the DNA with the biotinylated probe and developing the hybridized product with strepdavidin.

24. The process according to claim 6, wherein the oligonucleotide has one of the following sequences:

(a) oligonucleotide
(GATA)$_4$GA
ATA(GATA)$_3$GAG
TA(GATA)$_3$GAGA
A(GATA)$_3$GAGAT
(GATA)$_3$GA(GATA)
ATA(GATA)$_2$GA(GATA)G
TA(GATA)$_2$GA(GATA)GA
A(GATA)$_2$GA(GATA)GAT
(GATA)$_2$GA(GATA)$_2$
ATA(GATA)GA(GATA)$_2$G
TA(GATA)GA(GATA)$_2$GA
A(GATA)GA(GATA)$_2$GAT
(GATA)GA(GATA)$_3$
ATAGA(GATA)$_3$G
TAGA(GATA)$_3$GA
AGA(GATA)$_3$GAT
GA(GATA)$_4$
A(GATA)$_4$G
(GATA)$_4$GA or its complement sequence
TC(TATC)$_4$
C(TATC)$_4$T
(TATC)$_4$TC
ATC(TATC)$_3$TCT
TC(TATC)$_3$TCTA
C(TATC)$_3$TCTAT
(TATC)$_3$TC(TATC)
ATC(TATC)$_2$TC(TATC)T
TC(TATC)$_2$TC(TATC)TA
C(TATC)$_2$TC(TATC)TAT
(TATC)$_2$TC(TATC)$_2$
ATC(TATC)TC(TATC)$_2$T
TC(TATC)TC(TATC)$_2$TA
C(TATC)TC(TATC)$_2$TAT
(TATC)TC(TATC)$_3$
ATCTC(TATC)$_3$T
TCTC(TATC)$_3$TA
CTC(TATC)$_3$TAT
TC(TATC)$_4$ (b) oligonucleotide (GATA)$_5$
ATA(GATA)$_4$G
TA(GATA)$_4$GA
A(GATA)$_4$GAT
(GATA)$_5$ or its complement sequence (TATC)$_5$
ATC(TATC)$_4$T
TC(TATC)$_4$TA
C(TATC)$_4$TAT
(TATC)$_5$ (c) oligonucleotide
ATA(GATA)GACA(GATA)$_2$G
TA(GATA)GACA(GATA)$_2$GA
A(GATA)GACA(GATA)$_2$GAT
(GATA)GACA(GATA)$_3$
ATAGACA(GATA)$_3$G
TAGACA(GATA)$_3$GA
AGACA(GATA)$_3$GAT
GACA(GATA)$_4$
ACA(GATA)$_4$G
CA(GATA)$_4$GA
A(GATA)$_4$GAC
(GATA)$_4$GACA
ATA(GATA)$_3$GACAG
TA(GATA)$_3$GACAGA
A(GATA)$_3$GACAGAT
(GATA)$_3$GACA(GATA)
ATA(GATA)$_2$GACA(GATA)G
TA(GATA)$_2$GACA(GATA)GA
A(GATA)$_2$GACA(GATA)GAT
(GATA)$_2$GACA(GATA)$_2$ or its complement sequence
(TATC)$_2$TGTC(TATC)$_2$
ATC(TATC)TGTC(TATC)$_2$T
TC(TATC)TGTC(TATC)$_2$TA
C(TATC)TGTC(TATC)$_2$TAT
(TATC)TAGTC(TATC)$_3$
ATCTGTC(TATC)$_3$T
TCTGTC(TATC)$_3$TA
CTGTC(TATC)$_3$TAT
TGTC(TATC)$_4$
GTC(TATC)$_4$T
TC(TATC)$_4$TG
C(TATC)$_4$TGT
(TATC)$_4$TGTC
ATC(TATC)$_3$TGTCT
TC(TATC)$_3$TGTCTA
C(TATC)$_3$TGTCTAT
(TATC)$_3$TGTCTATC
ATC(TATC)$_2$TGTCTATCT
TC(TATC)$_2$TGTCTATCTA
C(TATC)$_2$TGTCTATCTAT
(TATC)$_4$TGTC(TATC)$_2$ (d) oligonucleotide (GATA)$_4$
ATA(GATA)$_3$G
TA(GATA)$_3$GA
A(GATA)$_3$GAT
(GATA)$_4$
(GACA)$_4$
ACA(GACA)$_3$G
CA(GACA)$_3$GA
A(GACA)$_3$GAC
(GACA)$_4$ or its complement sequence (TATC)$_4$
ATC(TATC)$_3$T
TC(TATC)$_3$TA
C(TATC)$_3$TAT
(TATC)$_4$
(TGTC)$_4$
GTC(TGTC)$_3$T
TC(TGTC)$_3$TG
C(TGTC)$_3$TGT
(TGTC)$_4$ (e) oligonucleotide (GGAT)$_4$
GAT(GGAT)$_3$G
AT(GGAT)$_3$GG
T(GGAT)$_3$GGA
(GGAT)$_4$ or its complement sequence (ATCC)$_4$
TCC(ATCC)$_3$A
CC(ATCC)$_3$AT
C(ATCC)$_3$ATC
(ATCC)$_4$ 25. The process according to claim 15, wherein the oligonucleotide is (CCT)$_5$ or (CTC)$_5$ or their complement sequences (AGG)$_5$ or (GAG)$_5$, respectively.

26. The process according to claim 19, wherein the oligonucleotide is (TG)$_8$ or its complement sequence (CA)$_8$ or is (TC)$_8$ or its complement sequence (GA)$_8$, respectively.

* * * * *